United States Patent [19]

Hiiesalu

[11] Patent Number: 4,989,453
[45] Date of Patent: Feb. 5, 1991

[54] BATTERY CONDITION INDICATOR

[76] Inventor: Alan Hiiesalu, 322 N. Lima St., Burbank, Calif. 91505

[21] Appl. No.: 435,602

[22] Filed: Nov. 6, 1989

[51] Int. Cl.$^5$ .............................................. G01N 9/10
[52] U.S. Cl. ...................................... 73/440; 429/91; 73/447; 73/291; 73/454
[58] Field of Search ................. 73/440, 311, 444, 448; 116/228; 429/91

[56] References Cited

U.S. PATENT DOCUMENTS 4,074,025 2/1978 Miyagawa ............................ 429/91
4,240,282 12/1980 Nelsen .................................. 73/447

FOREIGN PATENT DOCUMENTS 1528060 4/1966 France .................................. 73/280
2116327 9/1983 United Kingdom .................. 73/440

Primary Examiner—Hezron E. Williams
Assistant Examiner—Craig Miller
Attorney, Agent, or Firm—Gilbert Kivenson

[57] ABSTRACT

A battery condition readout device is disclosed. A series of slides of varying densities float or sink according to the amount of charge. An optical system permits slide position to be seen at a point external to the battery.

4 Claims, 2 Drawing Sheets

BATTERY CONDITION INDICATOR

BACKGROUND AND OBJECTIVES OF THE INVENTION

The present invention relates to a device which is mounted in a storage battery to measure electrolyte concentration and also indicate low electrolyte level. The invention will provide a motorist or mechanic with a quick visual check of the electrical charge and will warn of low liquid level in the battery. In this way any deterioration caused by aging or a faulty charging system can be readily detected and remedied.

The invention utilizes differentially-weighted, floatable slides and an optical system through which the position of the slides can be viewed from a point outside the battery. When the battery is fully charged, all the slides float. This corresponds to maximum concentration and density of the battery's electrolyte. A caption on the slide nearest the optical system appears in a window mounted in the top surface of the battery. As the battery discharges, the density of the electrolyte decreases; the differentially-weighted slides sink in succession. The captions on these slides appear one by one in the window. When the battery is completely discharged, the last slide—which has a density slightly less than that of water—remains floating and its caption indicates the discharge state of the battery. Should the electrolyte evaporate or leak to a dangerously low level, however, all the slides will sink; this exposes a low level caption placed on a hitherto occluded wall of the slide container.

It is one objective of the present invention to indicate in words the condition of charge of a storage battery.

It is a second objective of the present invention to utilize slides which float or sink according to the condition of the electrolyte and according to its level.

It is a further objective of the present invention to provide a simple and accurate method for economically producing the slides required in the construction.

These and other objectives are met by the invention to be explained in the appended description and the drawings.

DESCRIPTION OF THE PRIOR ART

It has been the previous practice to use an adaptation of the floating ball hydrometer in conjunction with a light conducting tube installed in place of one of the fill caps of a storage battery. If the battery is charged, a brightly colored ball can be seen at the end of the tube. The ball's density is adjusted so that it floats when the battery is fully charged. This is the working principle of U.S. Pat. Nos. 3,093,516, 3,218,857, 3,895,964, 3,915,753 and 4,308,817. Full charge or full level are the only conditions indicated. Intermediate readings which could be used for diagnosis are not provided. The device described by Miyagawa (U.S. Pat. No. 4,074,025) uses swinging vanes to indicate an intermediate charge but only color changes are displayed. The user must retain the meanings of the various colors in memory or refer to a chart. This is a difficult task when a large number of color schemes are employed by various battery manufacturers. The present invention identifies battery condition by name so that changes can be directly noted.

In the prior art the density of floating body must be calibrated—a time consuming operation. Adjustment of slide density in the present invention can be done quickly and accurately in a large scale manufacturing operation.

DESCRIPTION OF THE INVENTION

Figure 1:
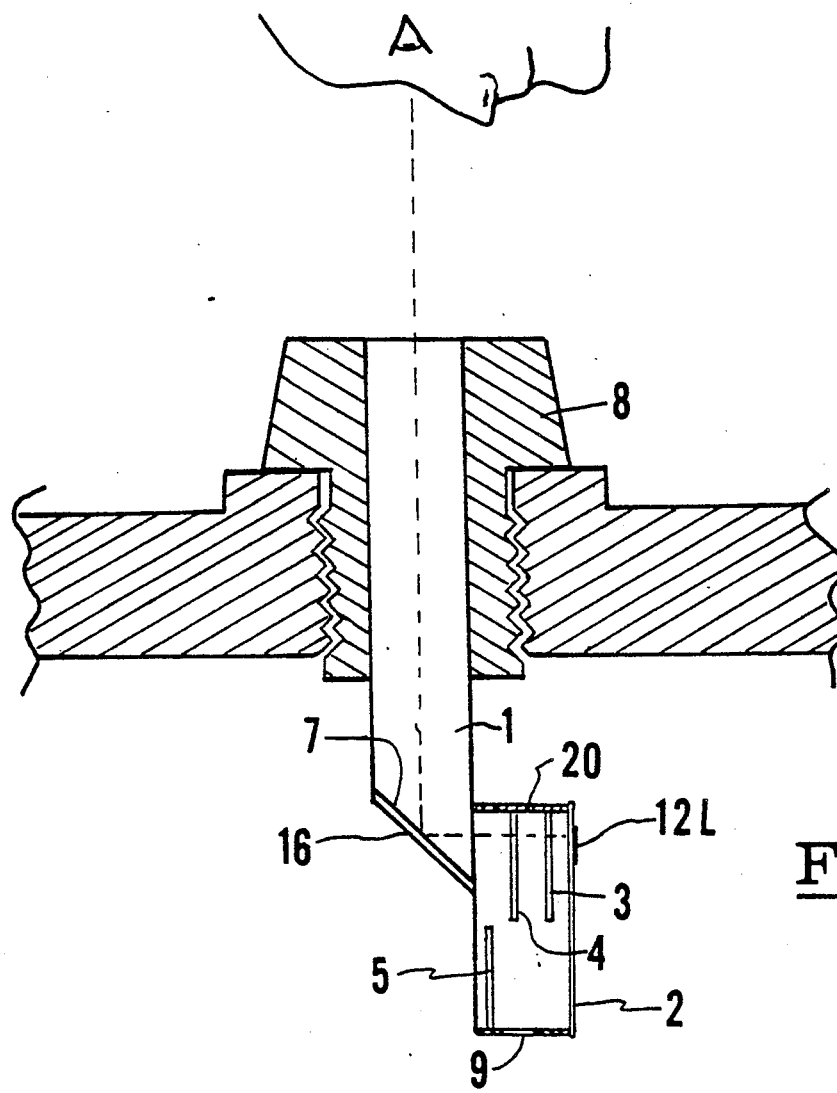
FIG. 1 is a cutaway, side view of the invention as it would be mounted in a storage battery.
Figure 2:
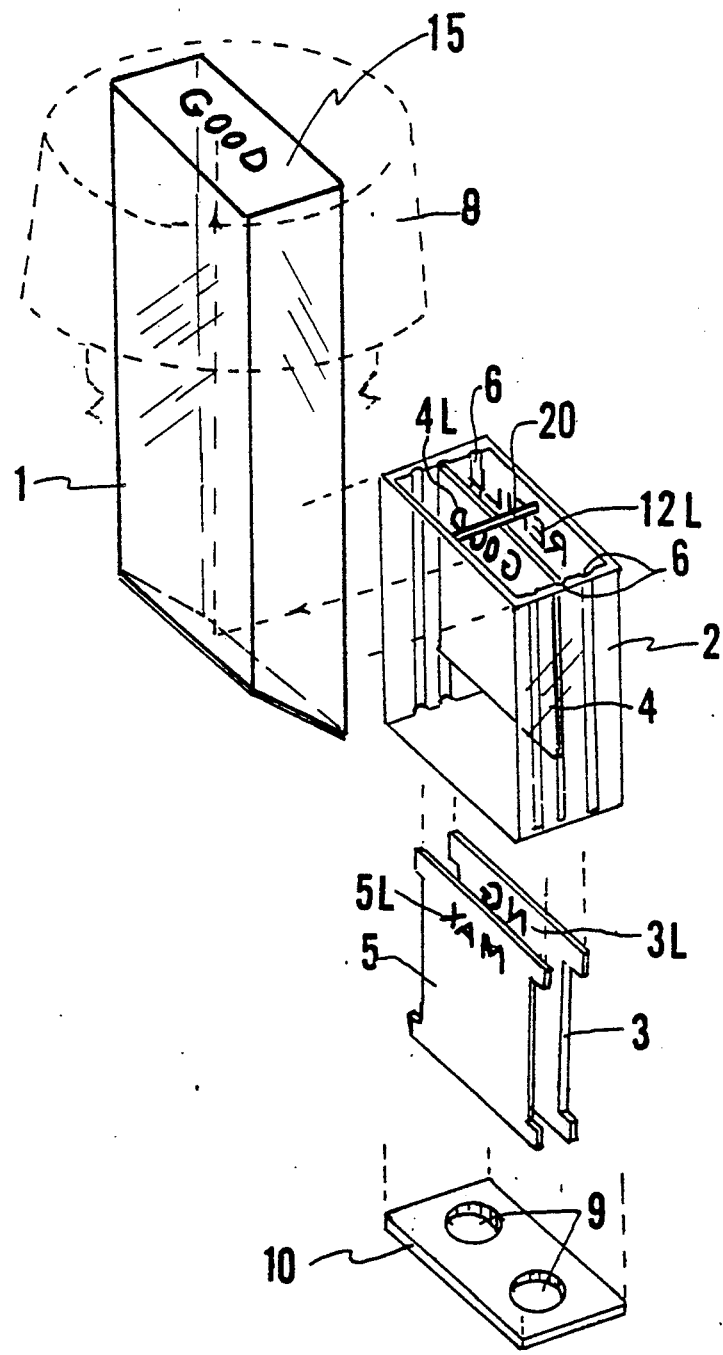
FIG. 2 is an expanded, isometric view of the invention.

A preferred embodiment of the invention, as shown in FIGS. 1 and 2, is made up of the rectangular, transparent body 1 to which is attached the slide container 2. Body 1 is polished flat on its top surface and is formed and polished at a 45 degree angle at its bottom. Surface 7 is preferably mirrored to enhance reflection and to prevent refractive loss of light when body 2 is immersed in battery electrolyte.

The slides 3, 4 and 5 are of successively increasing densities and can move vertically along grooves formed inside container 2. The transparent body 1 is sealed into plug 8 which is threaded to fit a standard battery fill port. Plug 8 may also be provided with friction-fit surfaces to slide into a standard friction-fit port used in some battery types. If the invention is to be incorporated during the manufacture of the battery, it can be provided with a specially drilled port.

Further details of the invention can be explained with reference to FIG. 2. The container 2 is open at the top and closed at the bottom by plate 10. Holes 9 in these plates permit circulation of battery electrolyte into and out of container 2 and also allow the escape of gas bubbles.

The slides 3, 4 and 5 are of increasing densities so that they will float in increasing concentrations of the electrolyte. Tabs 14 on the slides contact the grooves 6 so that rubbing friction during ascent and descent is minimized. Each slide bears a caption—3L, 4L, 5L, etc. which indicates the amount of chrage the battery must have inorder for that particular slide to float. When a slide is floating, its caption is reflected by the mirrored surface 7 to the viewing surface 15. A coasting 16 protects the mirror from contact with the electrolyte. When the battery is fully charged, all the slides float. In this case, the caption of the slide nearest the mirror is seen at the viewing surface 15. A suitable caption for slide 5 might be "Max" or "Chrgde". When the battery is partially discharged, slide 5 sinks but the others remain floating. The second slide's caption 4L is now visible in the viewing surface 15. A suitable caption for slide 4 might be "Fair", "Med" or "OK". If the battery charge decreases still further, slide 4 sinks but slide 3 remains floating. Caption 3L might read "Dischrgd", "NG" or "RPLC". Slide 3 has a density slightly less than that of water and will remain floating at any charge. If all the slides drop to the bottom of container 2—as would be the case if the electrolyte level were to drop sufficiently—the caption 12L placed on the rear wall of the container 2 would appear on the surface 15. A suitable caption of 12L might be "Refill" or "Lo Lvl". The above description is based on the use of three floats; more or fewer floats can be incorporated in the design to be adaptable to a particular battery and its application.

Figure 3:
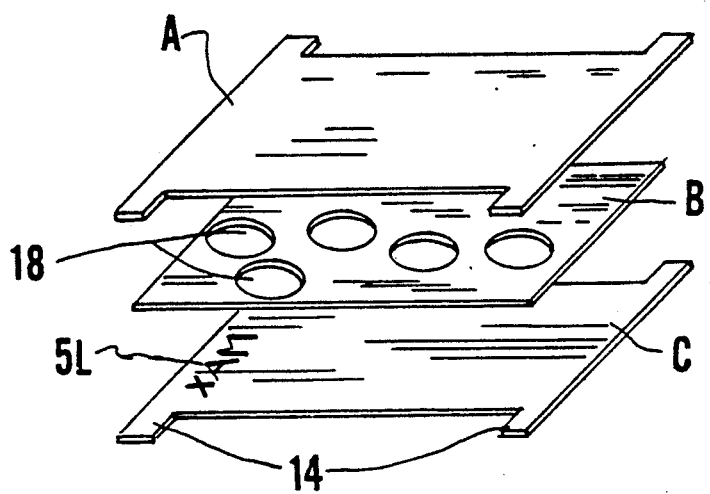
FIG. 3 is an expanded, isometric view of one of the floatable, indicating slides showing a preferred method of construction.

An accurate and low cost method of slide construction is shown in FIG. 3. Each slide is made up of a lower layer c, a transparent upper layer a and a perforated, transparent center layer b. The materials used may be transparent plastic or glass. The density may be adjusted by variations in the number and diameter of the holes 18. The layers can be cemented together or, with certain materials, pressure-sealed together. The captions, e.g. 5L, are imprinted on the bottom layer c so that they are protected from exposure to battery electrolyte by the lamination process. Protection for the caption 12L is provided by applying an acid resistant coating. In large scale production of the slides, the layers a and c can be stamped or injection molded. The center layer b can be produced by a hole punch and a stock of various density center layers produced. The relation between slide density and the number and diameter of holes is given by:

$$D_s = \left(1 - \frac{n\pi d^2}{12\ lw}\right) D_m$$

where
 $D_s$ = density of the assembled slide
 n = number of holes
 d = diameter of each hole
 l = length of slide
 w = width of slide
 $D_m$ = density of slide construction material.

A cross bar 20 retains the slides at the top of their travel when the battery is fully charged.

I claim:

1. An indicator for the continuous monitoring of electrolytic density in a storage battery from a point external to the battery comprised of:
   a. light transmitting means extending from the top of the battery to below the level of the electrolyte normally maintained in the battery, said light transmitting means being provided with a reflector at its lower end to permit an orthogonal view under and parallel to the surface of said electrolyte;
   b. a transparent slide container attached to a lower vertical surface of the light transmitting means in a position to be viewable through said reflector and having inlet and outlet holes to permit free entry and exit of battery electrolyte and the venting of gases;
   c. a number of vertically oriented, partially-hollow slides of varying weights and arranged in succession according to decreasing density and provided with restraints to move vertically when subjected to flotation forces by the battery electrolyte;
   d. captions affixed to each slide and a vertical surface of said slide container;
   whereby, when the indicator is installed in a storage battery so that the slide container and its contents are immersed in the electrolyte, the number of slides which float is an indication of the electrolyte density and the battery charge, the absence of slide flotation is indicative of low electrolyte level and the condition of the battery can be judged by the caption seen at the end of the light transmitting means.

2. An indicator as set forth in claim 1 in which said light transmitting means is a transparent solid, preferably rectangular in its cross section which has a flat upper surface and a sloping, mirrored lower end whereby a view through said transparent, slide container and its contents can be obtained by inspection of said flat upper surface.

3. An indicator as set forth in claim 1 in which the partially hollow slides are prepared by laminating two outer, solid layers of a transparent material with an inner layer containing a number of perforations, the diameter and the total sum of the perforations determining the density of the prepared slide.

4. An indicator as set forth in claim 1 in which said restraints to assure vertical movement of the slide under flotation forces can be vertical grooves formed into two opposing surfaces of said container, each slide being positioned loosely in the grooves, this positioning having the effect of restricting slide motion in any but a vertical plane.

* * * * *